United States Patent [19]

Landaburu et al.

[11] Patent Number: 4,478,829
[45] Date of Patent: Oct. 23, 1984

[54] PHARMACEUTICAL PREPARATION CONTAINING PURIFIED FIBRONECTIN

[75] Inventors: Ricardo H. Landaburu, Rye Town; Robert H. Yue, Floral Park; David L. Farb, LeGrangeville, all of N.Y.; Bernard N. Violand, Chesterfield, Mo.

[73] Assignee: Armour Pharmaceutical Company, Tarrytown, N.Y.

[21] Appl. No.: 595,100

[22] Filed: Mar. 30, 1984

Related U.S. Application Data

[63] Continuation-in-part of Ser. No. 489,624, Apr. 28, 1983, abandoned.

[51] Int. Cl.³ .................. A61K 37/02; A61K 35/14
[52] U.S. Cl. .................................... 424/177; 424/101
[58] Field of Search ........................... 424/177, 101

[56] References Cited

U.S. PATENT DOCUMENTS

| | | |
|---|---|---|
| 2,848,529 | 5/1980 | Schwinn et al. |
| 3,057,781 | 10/1962 | Mace et al. .................. 424/101 |
| 3,133,001 | 5/1964 | Muset et al. .................. 435/188 |
| 3,215,685 | 11/1965 | Nakanishi et al. ............ 424/176 |
| 3,607,858 | 9/1971 | Querry ........................ 424/177 |
| 4,089,944 | 5/1978 | Thomas ........................ 424/101 |
| 4,186,192 | 1/1980 | Lundblad et al. ............ 424/85 |

OTHER PUBLICATIONS

Carter and Hakomori, A New Cell Surface, Detergent-insoluble Glycoprotein Matrix of Human and Hamster Fibroblasts, J. Biol. Chem., 1981, 256(13), 6953-60, (Chem. Ab., vol. 95, p. 227).

*Primary Examiner*—Donald B. Moyer
*Assistant Examiner*—J. M. Stone

[57] ABSTRACT

Disclosed are readily reconstitutable lyophilized fibronectin formulations containing fibronectin, a neutral salt, a carbohydrate and a surface active agent.

3 Claims, No Drawings

PHARMACEUTICAL PREPARATION CONTAINING PURIFIED FIBRONECTIN

BACKGROUND OF THE INVENTION

This invention is a continuation-in-part of application Ser. No. 489,624 filed Apr. 28, 1983, now abandoned.

1. Field of the Invention

This invention relates to a stable pharmaceutical composition containing fibronectin. More particularly, the invention relates to a stable freeze-dried solid composition containing fibronectin which can be readily reconstituted.

Fibronectin is a large complex protein possessing important biological activities as a structural component of tissues and as a protein modulating and controlling the function of cells in the body in ways that range from normal growth to repair of damage and participation in the defense against invading foreign substances and organisms. It is known by a variety of names that reflect its diverse biological activities including the names of: large external transformation sensitive protein (LETS); cell surface protein (CSP); cell adhesion protein (CAP); opsonic $\mu_2$ surface binding glycoprotein; and cold insoluble globulin (CIG). Pharmacological application of fibronectin includes treatment of septic shock and treatment of infective diseases. Due to its action of enhancing intercellular adhesive properties and its effect on the morphology of cancer cells, fibronectin is a potential candidate for cancer treatment.

Fibronectin is obtained from fractions of plasma protein or fibroblast culture fluid, purified and pasteurized to eliminate the risk of contamination by viruses, and formulated for clinical application.

To be suitable for clinical application, fibronectin must be in a readily injectible or infusable form, must possess a high degree of therapeutic activity, must be stable on storage prior to use and must be homogeneous at the time of injection without aggregated particles or precipitates therein.

2. DESCRIPTION OF THE PRIOR ART

Purified fibronectin obtained by many techniques of purification common to the art is unstable in liquid media, undergoing progressive molecular decomposition on prolonged storage unless it is stored in the frozen state. The decomposition is accelerated by room and elevated temperatures resulting in hydrolysis and formation into discrete fragments of the polypeptide structure. The loss of therapeutic activity due to decomposition is substantial even within a few weeks rendering the composition ineffective for the intended purpose. Instability may be due to the presence of trace quantities of a proteolytic enzyme which may not be completely removed in the purification of the fibronectin. To stabilize fibronectin and prevent loss of therapeutic activity therein, fibronectin preparations are lyophilized for storage and reconstituted prior to injection or infusion into the patient. While lyophilization has been found effective in preventing the undesirable decomposition, it created a problem with reconstitution: fibronectin at low temperatures precipitates, hence the name cold insoluble globulin, and on reconstitution in aqueous media a portion of fibronectin remains precipitated requiring extended time periods for dissolution. This is undesirable to both patient and personnel administering the fibronectin, since time is of considerable importance for proper treatment of various conditions. Also, it is left to chance that health care personnel will uniformly insure complete dissolution of fibronectin in each vial containing unit dosages prior to administration to patients.

It is known to use stabilizing agents in protein preparations in order to prevent denaturation or other alteration of the proteins. Such stabilizers include albumin, amino acids, gelatin, glycine, and various sugars. It is also known that some of these stabilizing agents enhance the solubility and help prevent aggregation of some freeze dried proteins upon reconstitution.

While such stabilizing agents are used to advantage in certain protein formulations, they do not always lend a solution to the problems associated with freeze dried fibronectin preparations, namely, problems of stability, therapeutic activity and reconstitution.

It is, therefore, an object of the present invention to provide a stabile pharmaceutical fibronectin preparation which can be frozen and dried by the method of lyophilization.

It is another object of the present invention to provide a stable lyophilized pharmaceutical fibronectin preparation which can easily be reconstituted in aqueous media for administration to the patient.

It is still another object of the present invention to provide preparations containing fibronectin in unaltered form in the reconstituting media.

Other objects of the present invention will be apparent from the description that follows.

SUMMARY OF THE INVENTION

The foregoing and other objects of the present invention are accomplished in a preparation comprising:
  an aqueous solution of fibronectin;
  a neutral salt to adjust osmolar concentration;
  a carbohydrate; and
  a surface active agent.

Additionally, a buffer salt is used to control pH of the media. The preferred buffer salt is sodium citrate, which in small quantities enhances solubility of fibronectin and also possesses mild chelating properties helping to prevent fibronectin polymerization.

In general, the purified and pasteurized fibronectin in an aqueous solution containing the above-described ingredients is lyophilized into a solid in suitable containers and stored. Prior to use, the solid is reconstituted with sterile water.

DETAILED DESCRIPTION OF THE INVENTION

Sources of Starting Material

The active component of the therapeutic formulations of the present invention can be isolated from human plasma, the cryoprecipitate fraction, Cohn Fraction I or Cohn Fraction I-O of human plasma.

For therapeutic purposes, it is desirable to start with fibronectin solutions that are pasteurized in order to inactivate potential hepatitus virus. The prior art teaches that large amounts of amino acids, sugars or neutral carboxylic acids are effective stabilizers for protein solutions during pasteurization at 50° to 80° C. for 5 to 20 hours (such as thought by The Green Cross Corp., European Pat. No. 0058993 and Cutter Laboratories, Inc., European Pat. No. 0035204.) Purification of fibronectin by chromotography using gelatin coupled to agarose beads is also known: E. Engvall and E. Ruoslahti, 1977, Int. J. Cancer 20, 1; Cutter Laboratories, Inc., European Pat. No. 0035202. A purity of at least 95% and concentrations between 5 and 20 mg/ml are characteristic of this technology. Alternately, much less concentrated material of similar purity is commercially available from Calbiochem-Behring Corp., California Medical Chemistry, Collaborative Research Lab., Bethesda Research Laboratory, and Sigma Chemical Company. Although the existing commercially lyophilized preparations fail to reconstitute completely upon the addition of water, they represent sufficiently pure human fibronectin solutions which can be further concentrated in aqueous solution by the gelatin-agarose chromotographic technique:

(a) Mixing a pasteurized solution containing human fibronectin with agarose beads that are coupled with gelatin;
(b) Washing the immobilized fibronectin with a neutral aqueous buffer to remove contaminant proteins, if present;
(c) Eluting of at least 95% pure human fibronectin by using urea or 1 to 2M salt solution.

Purity is determined by the method "SDS Polyacylamide Gel Electrophoresis," U. K. Laemmli, Nature 227 680–685 (1970). Representative purities obtained by this method on materials used in the present invention were 96–97% and higher.

Formulation

Ordinarily, both the commercially available fibronectin and gelatin agarose processed human fibronectin contain excessive salt and buffer which are undesirable in an intravenous therapeutic product. Various methods are known that enable one skilled in the art to exchange the buffers and salts in a proteinaceous solution, thereby substituting ingredients that are desirable for human infusion. Purified and pasteurized fibronectin, which had been concentrated by gelatin-agarose chromotography, can be desalted by chromatography through a hydrophilic gel media, such as cross-linked dextran. The resulting fibronectin can be eluted in an aqueous solution containing from 0.05 to 0.075M NaCl and from 0 to 0.002M sodium citrate at a concentration of 3 to 16 mg fibronectin/ml.

Stabilization/Lyophilization

As previously noted, highly purified solutions of fibronectin in which fibronectin comprises at least 95% of the dissolved proteinaceous solids undergo molecular decomposition on extended storage in liquid media. The decomposition is progressive with time and is accelerated by room and elevated temperatures. While the mechanism of decomposition is not well understood, the resultant preparation containing fragments of fibronectin is not well-suited for clinical use. Lyophilization on the other hand, prevents such decomposition and is, therefore, an effective means for preserving the biological properties of fibronectin. Table I illustrates the typical result obtained on analysis of the respective solutions.

TABLE I

| Decomposition of Fibronectin with Time at 20° C. | | | |
|---|---|---|---|
| | After 1 wk. | After 1 mo. | After 3 mos. |
| Aqueous solution of fibronectin | 5% | 30% | 100% |
| Lyophilized fibronectin | 0 | 0 | 0 |

It can be readily ascertained from the above results that lyophilization prevents decomposition of fibronectin on storage. However, upon trying to reconstitute the lyophilized fibronectin only partial dissolution is normally observed when the technology of the prior art is supplied. Tables II, III and IV illustrate dissolution results obtain by the use of prior art technology.

TABLE II

Samples containing 189 mg of fibronectin (Fn) in a aqueous buffer of 0.08M NaCl, 0.01M citrate, at pH 7.3, having 2.5% w/v sucrose, and amounts of albumin shown in the first column hereunder were lyophilized and then reconstituted with 50 ml of water. The amount of fibronectin which remains insoluble at various time intervals are shown.

| Albumin | Time In Minutes After Reconstitution | Amt. of Insoluble Fn In Suspension (mg) |
|---|---|---|
| 0 | 15 | 99 |
| | 30 | 99 |
| | 60 | 97 |
| 2 mg/ml | 15 | 23 |
| | 30 | 13 |
| | 60 | 11 |
| 5 mg/ml | 15 | 38 |
| | 30 | 28 |
| | 60 | 27 |
| 10 mg/ml | 15 | 34 |
| | 30 | 18 |
| | 60 | 18 |
| 20 mg/ml | 15 | 32 |
| | 30 | 18 |
| | 60 | 15 |

TABLE III

An aqueous solution of fibronectin (5.0 mg/ml of 95% pure fibronectin in aqueous 0.05M NaCl, 0.002M citrate, at pH 7.3) was aliquoted into 6 portions. The six portions were formulated respectively with: (1) 0.05M NaCl, 0.002M citrate, 1.5% glucose, (2) 0.05M NaCl, 0.002M citrate, 2.5% glucose, (3) 0.05M NaCl, 0.002M citrate, 1.5% fructose, (4) 0.05M NaCl, 0.002M citrate, 2.5% fructose, (5) 0.05M NaCl, 0.002M citrate, 2.5% sucrose and (6) 0.05M NaCl, 0.002M citrate, 5.0% sucrose. Each of these formulated fibronectin solutions was filtered through first a 0.45 $\mu$M filter and then a 0.22 $\mu$M filter. The filtered fibronectin solution was aliquoted to 50 ml in glass vials, frozen, then lyophilized. The lyophilized samples were then reconstituted with 50 ml of water. Aliquots were removed at 15 minutes and at 60 minutes after reconstitution and were diluted 20-fold with an aqueous solution of 0.15M NaCl, 0.05M glycine, 0.01M citrate, at pH 7.2 before the absorbance at 280 nm was determined in order to evaluate the amount of fibronectin in solution.

| Dissolution of Freeze-dried Fibronectin in Evacuated Vials, Containing 250 mg of Fibronectin, Reconstituted with 50 ml of Water. | | |
|---|---|---|
| Formulation | Time in Min. After Recon. | Amount of Insoluble Fn in Suspension (mg) |
| 1. 0.05 M NaCl, 0.002 M citrate, 1.5% glucose in water | 15 | 10 |
| | 60 | 6 |
| 2. 0.05 M NaCl, 0.002 M citrate, 2.5% glucose in water | 15 | 6 |
| | 60 | 6 |
| 3. 0.05 M NaCl, 0.002 M citrate, 1.5% fructose in water | 15 | 9 |
| | 60 | 6 |
| 4. 0.05 M NaCl, 0.002 M citrate, 2.5% fructose in water | 15 | 14 |
| | 60 | 6 |

-continued

Dissolution of Freeze-dried Fibronectin in Evacuated Vials, Containing 250 mg of Fibronectin, Reconstituted with 50 ml of Water.

| Formulation | Time in Min. After Recon. | Amount of Insoluble Fn in Suspension (mg) |
|---|---|---|
| 5. 0.05 M NaCl, 0.002 M citrate, 2.5% sucrose in water | 15 | 20 |
|  | 60 | 6 |
| 6. 0.05 M NaCl, 0.002 M citrate, 5.0% sucrose in water | 15 | 12 |
|  | 60 | 6 |

TABLE IV

A solution of fibronectin (5 mg/ml of fibronectin in aqueous 0.038M NaCl, 0.001M citrate, at pH 7.2) was aliquoted into 4 portions. The four portions were formulated respectively with (1) 0.02%, (2) 0.05%, (3) 0.10% and (4) 0.20% (oxy-1,2-ethanediyl)$_{20}$ mono-9-octa-decanoate sorbitan (Polysorbate 80). Individual vials were filled with 25 ml of the fibronectin solution and were lyophilized. The lyophilized fibronectin samples were reconstituted with 25 ml of water. Aliquots were removed at 15 minutes, 30 minutes and 60 minutes after reconstitution. The samples were diluted 50-fold with 0.90% NaCl and the absorbance of the diluted samples was measured at 280 nm in order to evaluate the amount of fibronectin in solution.

Dissolution of Freeze-dried Fibronectin in Evacuated Vials, Containing 125 mg of Fibronectin, Reconstituted with 25 ml of Water.

| Formulation | Time in Min. After Recon. | Amount of Insoluble Fn in Suspension (mg) |
|---|---|---|
| 1. 0.038 M NaCl, 0.001 M citrate, 0.02% Polysorbate 80, pH 7.2 in water | 15 | 65 |
|  | 30 | 53 |
|  | 60 | 30 |
| 2. 0.038 M NaCl, 0.001 M citrate, 0.05% Polysorbate 80, pH 7.2 in water | 15 | 64 |
|  | 30 | 43 |
|  | 60 | 23 |
| 3. 0.038 M NaCl, 0.001 M citrate, 0.10% Polysorbate 80, pH 7.2 in water | 15 | 64 |
|  | 30 | 38 |
|  | 60 | 20 |
| 4. 0.038 M NaCl, 0.001 M citrate, 0.20% Polysorbate 80, pH 7.2 in water | 15 | 65 |
|  | 30 | 53 |
|  | 60 | 24 |

Table II through IV illustrate that lyophilized fibronectin formulations of the prior art cannot be reconstituted within practical time periods without having present insoluable fibronectin in the suspension.

Formulas of the Present Invention

We have discovered that selected ingredients used in lyophilized formulations containing fibronectin enables full and complete solution of fibronectin in a short period of time, ranging from 2 to 10 minutes, and preferably to less than one minute. The reconstituted solution of fibronectin prepared in accordance with the present invention is safe and effective and may be injected or infused into patients in need of fibronectin.

A preferred embodiment of the invention comprises:

a., an aqueous solution containing about 1–16 mg/ml, preferably about 3–8 mg/ml, and most preferably about 4–6 mg/ml of at least 95% pure fibronectin;

b., 0.002M to 0.05M, preferably 0.005M to 0.02M of a physiologically acceptable buffer salt selected from the group consisting of sodium citrate, sodium glycinate, sodium phosphate, and tris(hydroxymethyl)aminomethane or mixtures thereof;

c., 0.03M to 0.09M, and preferably 0.04M to 0.08M of a neutral salt, such as sodium chloride, to adjust the osmolar concentration of the formula to that of the physiologic milieu of about 0.14M of sodium chloride.

d., about 2% to 10% w/v, and preferably about 3% to 7% w/v of a carbohydrate selected from the group consisting of monosaccharides and disaccharides including glucose, galactose, mannose, sucrose, lactose, maltose, mannitol, or sorbitol; and e., about 0.01% to 0.4% w/v, preferably 0.02% to 0.1% w/v of a pharmaceutically acceptable surface active agent selected from the group consisting of: polyoxyethylene sorbitan esters such as (oxy-1,2-ethanediyl)$_{20}$ monododecanoate sorbitan (Polysorbate 20, a laurate ester), (oxy-1,2-ethanediyl)$_{20}$ monohexadecanoate sorbitan (Polysorbitate 40, a palmitate ester), (oxy-1,2-ethanediyl)$_{20}$ monooctadecanoate sorbitan (Polysorbate 60, a stearate ester), (oxy-1,2-ethanediyl)$_{20}$ mono-9-octadecanoate sorbitan (Polysorbate 80, an oleate ester); polyethylene glycol p-isooctylphenyl ethers such as $\alpha$[4-(1,1,3,3-tetramethylbutyl)phenyl]-$\omega$-hydroxy(oxy-1,2-ethanediyl)$_{100}$ (Triton X100®); anionic agents such as bile salts (sodium taurocholate, sodium cholate, sodium deoxycholate and sodium glycocholate); and polyhydric alcohols with surface active properties such as $\alpha$-hydro-$\omega$-hydroxy(oxyethylene)$_7$(oxypropylene)$_{54}$(oxyethylene)$_7$ (Pluronic® F-68 or Poloxamer 188).

The above-described ingredients are admixed and the pH of the mixture is adjusted, using an acid or a base, to the value of 6.5–7.5 and preferably 6.8–7.3. The mixture is then lyophilized in suitable containers for storage.

The following examples and testing thereof will further illustrate the preparations of the present invention.

EXAMPLE 1

An aqueous solution of fibronectin (containing 4.5 mg/ml fibronectin, 0.075M NaCl, 0.02M citrate, at pH 7.3) was aliquoted into 8 vials. Each of the 8 vials contained 225 mg of fibronectin. The vials were labeled 1 through 8. To the vials was added respectively:
Vial 1—1.25 g glucose
Vial 2—1.25 g glucose, 25 mg Polysorbate 80
Vial 3—1.25 g glucose, 25 mg Poloxamer 188
Vial 4—1.25 g glucose, 25 mg Sodium Taurocholate
Vial 5—2.5 g sucrose
Vial 6—2.5 g sucrose, 25 mg Polysorbate 80
Vial 7—2.5% sucrose, 25 mg Poloxamer 188
Vial 8—2.5% sucrose, 25 mg Sodium Taurocholate After thorough mixing, the contents of the vials were lyophilized. The lyophilized samples were reconstituted with 50 ml of water and the amount of fibronectin in solution was determined by measuring the absorbance at 280 nm at the time indicated in Table V.

TABLE V

| Formulation | Time After Reconsititution | Amount of Insoluble Fn in Suspension (mg) |
|---|---|---|
| Vial 1 0.075 M NaCl, 0.002 M citrate, 2.5% glucose, pH 7.3 in water | 60 min. | 23 |
| Vial 2 0.075 M NaCl, 0.002 M citrate, 2.5% glucose, 0.05% Polysorbate 80, pH 7.3 in water | 16 min. 30 sec. | 0 |
| Vial 3 0.075 M NaCl, 0.002 M citrate, 2.5% glucose, 0.05% Poloxamer 188, pH 7.3 in water | 10 min. 15 sec. | 0 |
| Vial 4 0.075 M NaCl, 0.002 M citrate, 2.5% glucose, 0.05% Taurocholate, pH 7.3 in water | 34 min. 30 sec. | 0 |
| Vial 5 0.075 M NaCl, 0.002 M citrate, 5.0% sucrose, pH 7.3 in water | 60 min. | 47 |
| Vial 6 0.075 M NaCl, 0.002 M citrate, 5.0% sucrose, 0.05% Polysorbate 80, pH 7.3 in water | 3 min. 45 sec. | 0 |
| Vial 7 0.075 M NaCl, 0.002 M citrate, 5.0% sucrose, 0.05% Poloxamer 188, pH 7.3 in water | 5 min. 15 sec. | 0 |
| Vial 8 0.075 M NaCl, 0.002 M citrate, 5.0% sucrose, 0.05% Taurocholate, pH 7.3 in water | 6 min. 45 sec. | 0 |

EXAMPLE 2

To 13 liters of an aqueous solution containing about 7 mg/ml of fibronectin, 0.01M sodium citrate and 0.075M NaCl at pH 6.7 was added 0.5 Kg of parenteral grade glucose and 10 grams of Polysorbate 80. The solution was gently stirred until all components dissolved. The solution was then diluted to 20 liters with an aqueous buffer consisting of 0.01M sodium citrate, 0.075M NaCl at about pH 7.0. The pH of the resultant solution was verified to be between 6.8-7.3, then the solution was subjected to initial clarification on a non-sterile filter and then sterilized by passage through a sterile, bacterially retentive filter obtained from Millipore Corp. The sterile solution was then aseptically dispensed into glass vials, 50 ml per vial, fitted with an appropriate rubber stopper of the lyophilizing type. The vials were placed in a freezer, and after freezing, subjected to lyophilization by the procedure customarily used in the art.

EXAMPLE 3

To about 14 liters of an aqueous solution containing about 8.2 mg/ml of fibronectin, 6% w/v of sucrose, 0.005M sodium citrate, 0.005M sodium glycinate at a pH of 6.5 was added 135 gms of NaCl, and 7.5 gms of Polysorbate 80. After dissolution of the ingredients by stirring, the volume was adjusted to 15 liters with an aqueous buffer solution of 0.005M of sodium citrate and 0.005M of sodium glycinate at pH 7.2. The pH of the diluted solution was adjusted with dilute HCl and NaOH and was verified to be between 6.8-7.3. The solution was then further processed as described in Example 2.

EXAMPLE 4

Eight liters of an aqueous solution containing 7.6 mg/ml of gelatin-agarose purified fibronectin, 0.001M sodium citrate, and 0.16M NaCl at pH 7.0 was diluted two-fold with an aqueous buffer consisting of 0.01M sodium citrate, 5.0% w/v glucose and 0.10% Pluronic ®F-68 at pH 7.0. After stirring to obtain complete dissolution, the pH of the resultant solution was between 6.8-7.3. The solution was then further processed as described in Example 2.

EXAMPLE 5

An aqueous solution of 12 mg/ml fibronectin was obtained containing 8M urea and 0.01M sodium citrate at pH 7.2 from the gelatin-agarose process. The solution was processed over a 16 liter chromotographic column of Sephadex ®-G-25 equilibrated with an aqueous buffer solution containing 5.0% w/v sucrose, 0.05M NaCl, and 0.02M sodium citrate at pH 7.0. During chromatographic exchange of salt for the purified fibronectin solution it was diluted from the initial concentration of 12 mg/ml to about 8 mg/ml. Nine liters of this pooled solution was further diluted with three liters of 5% sucrose, 0.05M NaCl and 0.02M sodium citrate to obtain a fibronectin concentration of about 6 mg/ml. Six grams of Polysorbate 80 was added to the diluted solution with stirring. The pH of the resultant solution was between 6.8-7.3. The solution was further processed as described in Example 2.

EXAMPLE 6

To 5 liters of an aqueous solution containing 6.3 mg/ml purified fibronectin, 0.075M NaCl, 0.002M sodium citrate at pH 7.2 was added 0.325 Kg of parenteral grade maltose and 5.0 gms of Polysorbate-80. The ingredients were dissolved by gentle stirring. The solution was diluted to about 6.5 liters with an aqueous solution containing 0.01M sodium citrate, 0.075M NaCl at pH 7.0. The pH of the resultant solution was adjusted to 6.8-7.3 using dilute HCl and NaOH. The solution was further processed as described in Example 2.

EXAMPLE 7

To 6.3 liters of an aqueous solution containing 8.1 mg/ml of purified fibronectin, 0.002M sodium citrate and 0.05M NaCl at pH 7.2 was added 0.5 Kg of parenteral grade sucrose and 5 grams of sodium taurocholate. After mixing to dissolve the ingredients, the volume was adjusted to 10.0 liters with an aqueous solution containing 0.05M NaCl and 0.002M sodium citrate at pH 7.2. The solution was then further processed as described in Example 2.

EXAMPLE 8

To 5 liters of an aqueous solution containing 6.2 mg/ml of purified fibronectin, 0.002M sodium citrate, and 0.05M NaCl at pH 7.1 was added 0.30 Kg of parenteral grade sucrose and 3.0 gms of Pluronic ®F-68. The solution was mixed to dissolve the ingredients and the volume was adjusted to 6.1 liters with an aqueous solution containing 0.05M NaCl and 0.002M sodium citrate at pH 7.1. The pH of the solution was adjusted to 6.8–7.3 using dilute HCl and NaOH. The solution was then further processed as described in Example 2.

Compositions of the final formulas based on Examples 2–8 are presented in Table VI.

TABLE VI

| FORMULAS | 2 | 3 | 4 | 5 | 6 | 7 | 8 |
|---|---|---|---|---|---|---|---|
| Fibronectin | 4.5 mg/ml | 7.6 mg/ml | 3.8 mg/ml | 5.5 mg/ml | 5.1 mg/ml | 5.1 mg/ml | 5.1 mg/ml |
| Buffer salt | 0.01 M | 0.005 M citrate | 0.01 M | 0.02 M | 0.002 M | 0.002 M | 0.002 M |
|  | Citrate | 0.005 M glycine | Citrate | Citrate | Citrate | Citrate | Citrate |
| Neutral Salt (NaCl) | 0.075 M | 0.075 M | 0.08 M | 0.05 M | 0.075 M | 0.05 M | 0.05 M |
| Carbohydrate | 2.5% Glucose | 5.0% Sucrose | 5.0% Glucose | 5.0% Sucrose | 5.0% Maltose | 5.0% Sucrose | 5.0% Sucrose |
| Surfactant | PS-80 | PS-80 | Pluronic ® F-68 | PS-80 | PS-80 | Tauro-Cholate | Pluronic ® F-68 |
|  | 0.05% | 0.05% | 0.05% | 0.10% | 0.05% | 0.05% | 0.05% |

The following example describes the dosage form for human administration.

EXAMPLE 9

| Quantitative Composition of Human Fibronectin | |
|---|---|
| Ingredient | Amount per Container |
| Fibronectin, Human | 240 mg ± 35 mg |
| Sucrose | 2.5 gm ± 0.25 |
| Sodium Chloride | 0.146 gm ± 0.015 |
| Polysorbate 80 | 0.025 gm ± 0.003 |
| Sodium Citrate | 0.028 gm ± 0.003 |
| Water for Injection | 50 ml* |

*Removed during lyophilization

The lyophilized formulations of the present invention are easily reconstituted within a short time period prior to use.

It will be apparent to those skilled in the art that various changes and modifications may be made without departing from the spirit and scope of the present invention.

What is claimed is:

1. An improved lyophilized fibronectin preparation which is readily reconstitutable with sterile water containing on reconstitution:
   1–16 mg/ml of at least 95% pure fibronectin;
   0.002M to 0.05M of a physiologically acceptable buffer salt selected from the group consisting of sodium citrate, sodium glycinate, sodium phosphate or tris(hydroxymethyl)amino methane;
   0.03M to 0.09M of sodium chloride;
   about 2% to 10% w/v of a carbohydrate selected from the group consisting of glucose, galactose, mannose, sucrose, lactose, maltose, mannitol or sorbitol; wherein the improvement comprises the addition of
   0.01% to 0.4% w/v of a pharmaceutically acceptable surface active agent selected from the group consisting of (oxy-1,2-ethanediyl)$_{20}$ monododecanoate sorbitan, (oxy-1,2-ethanediyl)$_{20}$ monohexadecanoate sorbitan, (oxy-1,2-ethanediyl)$_{20}$ monooctadecanoate sorbitan, (oxy-1,2-ethanediyl)$_{20}$ mono-9-octadecanoate sorbitan, α[4-(1,1,3,3-tetramethylbutyl)-phenyl]-ω-hydroxy(oxy-1,2-ethanediyl)$_{100}$, sodium taurocholate, sodium cholate, sodium deoxycholate, sodium glycocholate and α-hydro-ω-hydroxy(oxyethylene)$_7$(oxypropylene)$_{54}$(oxyethylene)$_7$.

2. An improved lyophilized fibronectin preparation which is reconstitutable in 10 minutes with sterile water containing on reconstitution:
   1–16 mg/ml of at least 95% pure fibronectin;
   0.005M to 0.02M of a physiologically acceptable buffer salt selected from the group consisting of sodium citrate, sodium glycinate, sodium phosphate or tris (hydroxymethyl) amino methane;
   0.04M to 0.08M of sodium chloride;
   about 3% to 7% w/v of a carbohydrate selected from the group consisting of glucose, galactose, mannose, sucrose, lactose, maltose, mannitol or sorbitol; wherein the improvement comprises the addition of:
   0.02% to 0.1% w/v of a pharmaceutically acceptable surface active selected from the group consisting of (oxy-1,2-ethanediyl)$_{20}$ monododecanoate sorbitan, (oxy-1,2-ethanediyl)$_{20}$ monohexadecanoate sorbitan, (oxy-1,2-ethanediyl)$_{20}$ monooctadecanoate sorbitan, (oxy-1,2-ethanediyl)$_{20}$ mono-9-octadecanoate sorbitan, α[4-(1,1,3,3-tetramethylbutyl)phenyl]-ω-hydroxy(oxy-1,2-ethanediyl)$_{100}$, sodium taurocholate, sodium cholate, sodium deoxycholate, sodium glycocholate and α-hydro-ω-hydroxy(oxyethylene)$_7$-(oxypropylene)$_{54}$(oxyethylene)$_7$.

3. An improved fibronectin preparation in dosage form which is readily reconstitutable with 50 ml of sterile water containing on reconstitution:
   240±35 mg of at least 95% pure fibronectin;
   2.5±0.25 gm of sucrose;
   0.14±0.015 gm of sodium chloride;
   0.025±0.003 gm of sodium citrate; wherein the improvement comprises the addition of:
   0.025±0.003 gm of (oxy-1,2-ethanediyl) mono-9-octadecanoate sorbitan.

* * * * *